US 7,807,460 B2

(12) United States Patent
Shao et al.

(10) Patent No.: US 7,807,460 B2
(45) Date of Patent: Oct. 5, 2010

(54) EXPRESSION VECTOR SYSTEM REGULATED BY $\sigma^{32}$ AND METHODS FOR USING IT TO PRODUCE RECOMBINANT PROTEIN

(76) Inventors: Weilan Shao, 10 North Xianying Road, Tingquan V.39-1, Nanjing, Jiangsu 210046 (CN); Huawei Wu, 122 Ninghai Road, Nanjing, Jiangsu 210097 (CN); Jianjun Pei, Life Sciences, NJNU, 1 Wenyuan Road, Nanjing, Jiangsu 210046 (CN)

( * ) Notice: Subject to any disclaimer, the term of this patent is extended or adjusted under 35 U.S.C. 154(b) by 0 days.

(21) Appl. No.: 11/614,626

(22) Filed: Dec. 21, 2006

(65) Prior Publication Data

US 2007/0254335 A1    Nov. 1, 2007

Related U.S. Application Data

(63) Continuation-in-part of application No. PCT/CN2004/000742, filed on Jul. 5, 2004.

(51) Int. Cl.
*C12N 5/00* (2006.01)
*C12N 15/00* (2006.01)
*C12P 21/04* (2006.01)
*C07H 21/02* (2006.01)

(52) U.S. Cl. .................. 435/325; 435/320.1; 435/69.1; 536/23.1; 536/24.1

(58) Field of Classification Search ...................... None
See application file for complete search history.

(56) References Cited

OTHER PUBLICATIONS

Wegrzyn et al., Differential inhibition of transcription form sigma70 and sigma32 dependent promoters by rifampicin., 1998, FEBS Letters, vol. 440, pp. 172-174.*
Fayet et al., Suppression of the *Escherichia coli* dnaA46 mutation by amplification of the groES and groEL genes, Mol Gen Genet. Mar. 1986, vol. 202(3), pp. 435-445.*
Wang et al., Sigma 32-Dependent Promoter Activity In Vivo: Sequence Determinants of the groE Promoter, Journal of Bacteriology, Oct. 2003, vol. 185, pp. 5800-5806.*

* cited by examiner

*Primary Examiner*—David J Steadman
*Assistant Examiner*—Alexander D Kim
(74) *Attorney, Agent, or Firm*—Kening Li; Pinsent Masons LLP

(57) ABSTRACT

This invention discloses an expression vector system comprising a promoter recognized and regulated by a heat shock sigma factor of *E. coli*, especially $\sigma^{32}$. Preferably, the promoter comprises the consensus sequence of *E. coli* heat shock promoters as shown in SEQ ID NO:1. Also disclosed are methods for producing proteins using the promoter under heat shock conditions. Furthermore, the present invention discloses a method for creating a sudden temperature shift in a cell culture which has been pre-cultured to reach an optimal condition and which temperature shift will allow optimal production of a recombinant protein under the control a heat shock promoter.

7 Claims, 3 Drawing Sheets

A pHsh 2442bp

Hsh promoter
Hpal, Ncol
Sall, Stul
Xbal
rbs
Pstl
NotI
Amp^r
MCS
SphI
NsiI
His-tag
XhoI
HindIII
Hsh terminator
ColE1 ori

B

Hsh promoter
AAGCGGAAGAGCCCCCTTGAATGTGGGGAAACATCCCCATGAT

+1                                    rbs           NcoI
CCAATGACCTGTTAACCGTCGACAAGAAGGAGATATACCCATGG StuI  XbaI   PstI   NotI  SphI              XhoI
AGGCCTCTAGACTGCAGCGGCCGCATGCATATGGATCTCGAGCA His•tag         HindIII        Hsh terminator
CCACCACCACCACCACTAATAAGCTTGAAGGCCGCTTCCGAAA

GGAAGCGGCTTTTTG

US 7,807,460 B2

EXPRESSION VECTOR SYSTEM REGULATED BY $\sigma^{32}$ AND METHODS FOR USING IT TO PRODUCE RECOMBINANT PROTEIN

CROSS REFERENCE TO A RELATED APPLICATION

This application is a Continuation in Part of International Application No. PCT/CN04/000742 filed Jul. 5, 2004, the contents of which is incorporated herein by reference in its entirety.

FIELD OF THE INVENTION

The invention is in the field of genetic engineering, specifically relates to expression vectors controlled by a sigma factor $\sigma^{32}$ of *Escherichia coli*, and methods of expression of target genes using the vectors.

BACKGROUND OF THE INVENTION

In molecular biotechnology and bioengineering, the production of recombinant protein is achieved by cloning the target gene into an expression vector, and introducing the recombinant vector into corresponding host such as bacterium, yeast, plant or animal cells, where the target gene is expressed. Bacterial host *E. coli* is often the first choice for the expression of many recombinant proteins, because it is easy, fast and inexpensive to cultivate, and its vector systems have been well developed. To reach a high level of expression in *E. coli*, the foreign gene is usually under the control of a regulatory promoter, which plays important roles in reducing the adverse effects of recombinant protein on host cells, decreasing the degradation of target protein by cellular protease of the host cells, and increasing the production of active recombinant protein. Using promoters of different sources, many *E. coli* expression vector systems have been developed in the last 20 years, and the best known vectors are those containing lac promoter and its hybrids, the bacteriophage λ $p_L$ promoter and T7 promoter, which are respectively identified as the lac/tac/trc system, the $p_L$ system and the T7 system (Sambrook, J, and D W Russell. 2001. Molecular Cloning: a laboratory manual, 3rd ed. Cold Spring Harbor Laboratory Press, Cold Spring Harbor, N.Y.).

The lac/tac/trc system. In this expression system, vectors carry the lac promoter, or its hybrid tac or trc promoter. Under the control of one of these promoters, the transcription initiation of target gene is repressed by the repressor of lac opron in the absence of lactose or its analogues such as isopropyl-β-D-thiogalactopyranoside (IPTG). In both experimental and commercial production settings, the expression of target genes is induced by adding IPTG or lactose as the inducing agent into the culture of *E. coli* harboring vectors of the lac/tac/trc system, wherein the inducing agent releases the repressor and allows transcription to initiate. However, the high cost and toxicity of IPTG limites its wide use for the production of proteins for medical and many industrial applications. Lactose is cheaper than IPTG as inducing agent, but is not as effective as the latter because it can be metabolized.

The $p_L$ system. In bacteriophage λ, the early transcription promoters $p_L$ and $p_R$ are regulated by a repressor encoded by the cI gene. The $p_L$ has been used in expression vectors to control the expression of target genes via the gene product of cIts857, which is a temperature sensitive mutant of cI. In cells harboring these vectors, the repressor binds to $p_L$ and represses the transcription of target gene at low temperatures but not at elevated temperatures, and thus gene expression is induced by raising the temperature of a culture (Elvin C M, P R Thompson, M E Argall et al. 1990. Modified bacteriophage lambda promoter vectors for overproduction of proteins in *Escherichia coli*. Gene, 87: 123-126). However, because an effective induction requires rapidly raising the temperature from about 30° C. to 40° C., there is difficulty in the application of the $p_L$ system for large-scale cultures in industrial settings (Glazer, A N, and H Nikaido. 1995. Microbial Biotechnology. WH Freeman and Company, New York).

The T7 system. In this system, the bacteriophage T7 promoter is used in vectors to control the expression of target gene, and the transcription is specifically performed by T7 RNA polymerase. The gene encoding T7 RNA polymerase has been integrated in the chromosome of host cells under the control of lac or $p_L$ promoter, and its expression is induced by IPTG or temperature shift. The bacteriophage T7 promoter is the strongest among all the promoters used in *E. coli* expression systems, but growth inhibition or inclusion body formation sometimes are associated with high expression levels [Russell D. 1999. Gene expression systems based on bacteriophage T7 RNA polymerase. In Gene Expression Systems (Fernandez, J M, and J P Hoeffler, eds.), pp 9-44. Academic Press, London]. Meanwhile, the T7 system faces the same problems as other systems in inducing agents or raising temperatures.

The heat shock system of *E. coli*. When *E. coli* is subjected to a quick rise of temperature, an alternative sigma factor ($\sigma^{32}$, encoded by the rpoH gene) recognizes the so-called heat-shock promoters of a group of heat-shock protein-encoding genes, resulting in the expression of heat-shock proteins. The DNA sequences of heat-shock promoters have been known, and their consensus sequences are different from that of the general promoters recognized by the $\sigma^{70}$ (Miller, J H. 1992. A Short Course in Bacterial Genetics, Handbook. Cold Spring Harbor Laboratory Press, New York) (Turner, P C T, A G McLennan, A D Bates, and M R H White. 1997. Instant Notes in Molecular Biology, BIOS Scientific Publishers, UK). The differences of the two consensus sequences are shown below.

```
General promoters:           (SEQ ID NO: 11)
-----------TTGACA-16~18 bp-TATAAT Heat-shock promoters:        (SEQ ID NO: 12)
--C-C-CTTGAA-13~15 bp-CCCUCAT-T
```

Although the heat-shock system in *E. coli* has been well understood for its physiological functions and regulatory mechanisms, prior to the present invention, heat-shock promoters have never been used effectively as promoters to regulate the expression of foreign genes in plasmid vectors. This may be due to the fact that the heat-shock reaction lasts (i.e. the heat-shock system shuts down, and the cell is back to its normal state within 20 min) only 20 minutes after *E. coli* is subjected to an increase in temperature. Commercial application of this system may have also been discouraged by the apparent difficulty in quickly raising the temperature of large volume of culture medium, as in the case of using $p_L$ system.

SUMMARY OF THE INVENTION

The present invention provides an expression vector comprising promoters which are recognized and regulated by a heat shock sigma factor of *Escherichia coli*. Preferably, the heat shock sigma factor of *E. coli* is $\sigma^{32}$. An expression vector of the present invention preferably comprises a promoter that comprises the consensus sequence of bacterial heat shock promoters, especially that depicted as SEQ ID NO: 1.

In one embodiment, an expression vector of the present invention further comprises a polynucleotide sequence encoding a target polypeptide sequence under the control of the promoter. The expression vector according to the present invention is more preferably a plasmid vector, such as the pHsh vector shown in FIG. 1.

The present invention in another embodiment provides a method for producing a target polypeptide, the method comprising (1) providing bacterial cells harboring an expression vector which comprises a polynucleotide sequence encoding the polypeptide under the control of a promoter that is recognized by a heat shock sigma factor of *Escherichia coli*, and (2) cultivating the bacterial cells under conditions that induce the expression of the polynucleotide sequence in the vector. The bacterial cells are preferably *E. coli* cells. In one embodiment, the bacterial cells are subject to a temperature shift, or a heat shock.

The present invention further provides a method for creating a sudden temperature shift or heat shock in a cell culture, the method comprising: (1) providing a fermentor A and a fermentor B, wherein a heating rate for fermentor B is known, wherein the heating rate is defined as a time period needed for heating up a unit volume of cultural medium from about 30° C. to about 42° C., (2) cultivating cells of interest in a suitable amount of medium in fermentor A at 27° C.~35° C., (3) maintaining a suitable amount of cultural medium in fermentor B at about 37° C.~44° C.; (4) introducing medium in fermentor A alone with cells at suitable growth stage to fermentor B at a rate corresponding to the heating rate for fermentor B, wherein a unit volume of cultural medium is introduced to fermentor B per time period, while fermentor B is being heated at the heating rate; and (5) continuing to culture the cells in fermentor B at about 37° C.~44° C. The cells are preferably *E. coli* cells and a heat shock reaction is induced in the cells upon introduction from Fermentor A to Fermentor B. In preferred embodiments, the cells comprise an expression vector which comprises a promoter that is recognized and regulated by a heat shock sigma factor and a polynucleotide sequence encoding a polypeptide sequence under the control of the promoter, and wherein the polypeptide is expressed upon the induction of the heat shock reaction. Preferably, prior to step (4) above, the volume of cultural medium in fermentor B is between about 1/10 and equal amount of cultural medium in Fermentor A. A small amount of medium in fermentor B is preferred to ensure that the newly introduced cultural medium from fermentor A is quickly brought to the high temperature desired, and excessive volume in fermentor B prior to introduction of medium from fermentor A should be avoided such that the cells from the fermentor A not be too much diluted. Preferably, the immediately after step (4), cell density in fermentor B is about 10%~20% of the highest cell density reachable under the nutrient, aeration and other cultural conditions. Under these circumstances, the cells are cultured in fermentor B for an additional 6~9 h at 40° C.~42° C. after step (4) above so as to achieve maximum level of production for the target protein.

DETAILED DESCRIPTION OF THE INVENTION

Figure 1:
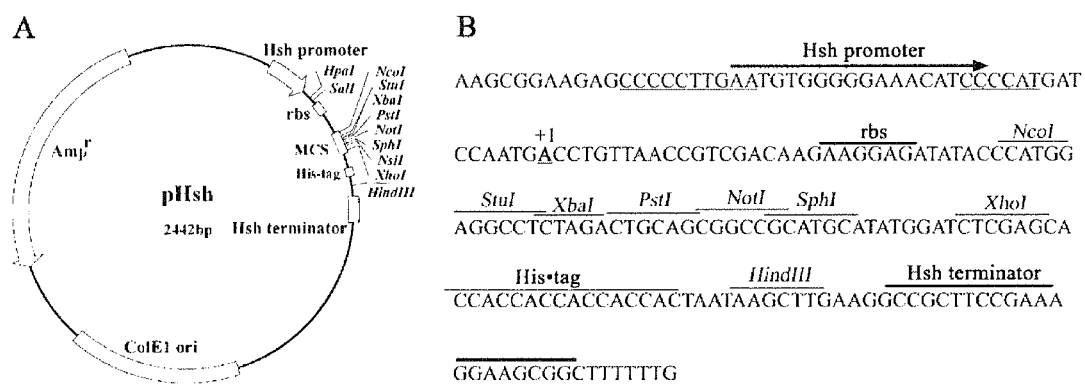
FIG. 1(A) depicts the structure of pHsh. The restriction sites listed in pHsh are unique for the respective endonucleases.
FIG. 1(B) shows the nucleotide sequence of the regulatory region in pHsh. (SEQ ID NO:10)

In one embodiment, the present invention provides a novel expression system for example of plasmid vectors, containing heat-shock promoters, in which the over-expression of target genes is regulated by $\sigma^{32}$. In another embodiment, the present invention provides a method of perform heat-shock induction of target gene expression, especially at the fermentor-scale by using the novel vectors.

Some of the preferred embodiments of the present invention are provided below:

1. A series of plasmid vectors or a vector system with promoters recognized and regulated by $\sigma^{32}$ of *Escherichia coli*. These vectors are designated as Hsh expression system.

2. Vectors described in '1', containing a promoter designed on the basis of the consensus sequence of heat-shock promoters, and regulated by $\sigma^{32}$. The preferred sequence of this promoter comprises 5'-<u>CCCCC</u> TTGAA TGTGG GGGAA ACAT<u>C CCCAT</u> GA<u>T</u>CC AAGGAG-3' (SEQ ID NO:1).

3. Vectors as described in '1' carrying one of heat-shock promoters from heat-shock protein-encoding genes of *E. coli*. The promoter sequences in these vectors include 5'-CGGCG TTGAA TGTGG GGGAA ACATC CCCAT ATACT GACGT-3' (SEQ ID NO:2) for lon gene, or 5'-CCCCC TTGAT GACGT GGTTT ACGAC CCCAT TTAGT AGTCA-3' (SEQ ID NO: 3) for dnaKP1 gene.

4. Recombinant plasmids constructed by inserting any polypeptide-encoding gene into any vector described in '1'. A target gene can be inserted into any vector described in '1', '2' or '3'.

5. A method for the production of recombinant proteins by using the gene expression vectors described in '1'. The procedures include inserting a gene into the vectors to construct recombinant plasmids as described in '4', transforming *E. coli* cells with constructed plasmids, and then cultivating the transformed cells and inducing the gene expression by a temperature shift.

6. A method for creating a quick temperature shift of the culture to obtain a heat-shock induction of foreign gene expression, which includes following steps:

(1) Providing two fermentors A and B, and determining the heating rate (time need for heating up a unit volume (e.g. a liter) of medium from about 30° C. to about 42° C. in fermentor B (minutes/liter).

(2) Adding a suitable amount of medium to fermentor A and B, and controlling the temperature of fermentor A at 27° C.~35° C., and fermentor B at 37° C.~44° C.

(3) Inoculating the medium in fermentor A with E. coli cells harboring recombinant plasmids, and cultivating at 27° C.~35° C. with aeration and stirring.

(4) When the cells reach early logarithmic phase, transferring the culture from fermentor A into fermentor B at a flow rate (liter/min) that matches the heating rate (min/liter) with continuous heating and stirring.

(5) After all the culture is transferred into fermentor B from fermentor A, continuing to cultivate for 2~12 h at 37° C.~44° C. The foreign gene is induced to express during this period.

7. The method for heat-shock induction of gene expression as described in 6, wherein in step (2), the starting volume of the medium in fermentor A and that in fermentor B are in the ratio of 10 to 1; and after autoclave, the temperature is set at 30° C. for fermentor A, and 40° C.~42° C. for fermentor B, in step (4), the culture in fermentor A is injected into fermentor B, which is under suitable heating and aeration, whereby the temperature of the culture shifts from 30° C. to 40° C.~42° C. instantaneously and the cell density ($OD_{600}$) is about 10%~20% of the highest reading to be reached under the conditions, and in step (5), after the culture has been transferred from fermentor A to fermentor B, the cell growth is continued for 6~9 h at 40° C.~42° C. to obtain large amount of recombinant proteins.

Advantages of Hsh Expression System

The gene expression in the plasmid vectors of Hsh system employs the regulation mechanism of the heat shock system of E. coli, while other expression systems are directly or indirectly regulated by repressors such as gene products of lacI and cI(ts)857. Although its transcription may not be as strong as bacteriophage promoters, Hsh promoter allows its plasmids to employ a replicon having a very high copy number. The Hsh expression system along with the induction methods of the present invention have at least the following advantages:

1. The expression vectors of Hsh system achieve high recombinant protein yield (U/liter or mg/liter).

2. Gene expression is induced by a temperature shift instead of costly chemical inducing agent such as IPTG, which may contaminate the recombinant protein product.

3. The methods for heat-shock induction allow the production of recombinant proteins in fermentor-scales.

4. The small molecule size of Hsh vectors allows the modification of the sequences of the target gene in situ.

5. There is no special host cell requirement due to genetype.

EXAMPLES

Example 1

Construction of Hsh Vectors

1. Design of Heat-Shock Promoters and Terminator

Based on the consensus sequence of heat-shock promoters in E. coli, a novel promoter was designed and used in most of Hsh vectors exemplified herein. The nucleotide sequence of this novel promoter comprises 5'-CCCCC TTGAA TGTGG GGGAA ACATC CCCAT GATCC AAGGA G-3' (SEQ ID NO:4), designated as Hsh promoter (FIG. 1). The promoters of the lon gene and the dnakP1 gene of E. coli were directly used to control the expression of foreign genes in some other Hsh vectors. The nucleotide sequence for the lon promoter is 5'-CGGCG TTGAA TGTGG GGGAA ACATC CCCAT ATACT GACGT-3' (SEQ ID NO:2), and 5'-CCCCC TTGAT GACGT GGTTT ACGAC CCCAT TTAGT AGTCA-3' (SEQ ID NO:3) for the dnakP1 promoter.

A ρ independent GAAA terminator was designed for pHsh vectors on the basis of ECORPSRPO of E. coli. Its nucleotide sequence comprises 5'-GAAGG CCGCT TCCGA AAGGA AGCGG CTTTT TT-3' (SEQ ID NO:5), which was named as Hsh terminator (FIG. 1). Other terminators from E. coli can also be used in these vectors to terminate transcriptions initiated by heat-shock promoters, e.g. the ECORPOC terminator (5'-CGGAC GTCAG GCCGC CAC TT CGGTG CGGTT ACGTC CGGCT TTCTT T-3') (SEQ ID NO:6) or the ECOXYLE terminator (5'-CTTCC TGTCC AGCAC GCCGC GCCAT TTCGG CGTGC TGACT TTTT-3') (SEQ ID NO:7).

2. The Amplification and Assembly of DNA Fragments (1) A pair of primers containing Hsh promoter or terminator were synthesized, the forward primer was 5'-CCGGA ATTCC TCCTT GGATC ATGGG GATGT TTCCC CCA-CATT CAAGG GGG<u>CTCTTCCGCTTCCTCTC</u>-3' (SEQ ID NO:8), and the reverse primer was 5'-TGAAG CTTGA AGGCC GCTTC CGAAA GGAAG CGGCT TTTTT <u>GCCTGATGCGGTATTTTC</u>-3' (SEQ ID NO:9), where underlined sequences anneal to the template pUC19. The PCR amplification was carried out with DNA polymerase Pyrobest (TaKaRa Biotech, Co., Ltd., Dalian, China), and the resulting fragments contained the replicon and the ampicillin resistance gene from pUC19 in addition to Hsh promoter and terminator.

(2) The xynB gene of Thermotoga maritima (ATCC43589) encoding a xylanase was amplified by PCR with addition of restriction site for BamHI at the 5' end, and sequences of XhoI, a 6-his-tag, and a restriction site for HindIII at the 3' end, respectively. The resulting fragments were digested by BamHI and HindIII and inserted into pAlter-ex2 which had been digested by the same restriction enzymes, and the recombinant plasmids obtained from transformed E. coli was designated as pAlter-ex2-xynB.

(3) A fragment containing the SD sequence, multiple cloning sites (MCS), xynB, his-tag sequence was cut out from pAlter-ex2-xynB by EcoRI and HindIII, and ligated to the fragment generated in (1) which had been digested with the same restriction enzymes. The resulting plasmid was designated as pHsh-xynB. The vector pHsh was obtained by removing xynB from pHsh-xynB with BamHI and XhoI, blunting the ends, and re-circulating the plasmids (FIG. 1)

The Hsh system of vectors of the present invention may comprise heat-shock promoters other than the Hsh promoter. For example, vector pHsh-lon or pHsh-dk was obtained by substituting the Hsh promoter in pHsh with the heat-shock promoter of gene ion or dnak p1. The procedures included the introduction of substituted sequences by PCR using the DNA polymerase of Pyrobest, phosphorylation and the self-ligation of the fragments.

Example 2

Methods for the Application of Hsh Vectors

1. Cloning and Modification of a Foreign Gene in the Vectors of Hsh System

A target gene suitable for expression using the Hsh system vectors of the present invention should encode a protein that is relatively stable at or above 42° C. Gene manipulation is performed following standard methods described in Molecular Cloning by Sambrook and Russell (2001). In brief, a target gene is amplified by PCR, the PCR products are digested with a proper restriction enzyme(s), ligated to a vector of Hsh system at the MCS, and introduced into E. coli cells. The recombinant plasmids are isolated from the transformed E. coli, and stored in freezers in the presence of 1 mM EDTA for further work.

After a gene is cloned into a vector of the Hsh system, site-directed mutagenesis can be performed in situ because the vector is small enough for reverse PCR using primers containing modified nucleotide sequences. In this case, high fidelity DNA polymerases such as Pyrobest may be employed to produce DNA fragments of blunt ends, which are then phosphorylated and re-circularized without the insertion or deletion of nucleotide. For example, xynB was modified (to remove the signal peptide from xynB and replace some codons which were rare in E. coli) in pHsh-xynB to generate pHsh-xynIII, which gave an increase of about 68 times in expression level.

2. Induction of Gene Expression in Test Tubes or Shaking-Bottles

In a laboratory setting, the induction of recombinant gene expression is often carried out in test tubes or shaking-bottles. Under these conditions, the expression of foreign gene using vectors regulated by temperature shift is an easy operation and avoids the need for IPTG. Because it requires a quick rise of the temperature for effective induction, in practice, a relatively small volume of culture in a container is recommended for rapid temperature exchanges, e.g. placing 3 ml or less medium in a test tube with a diameter of 16 mm, or less than 30 ml in a 100 ml-flask.

Working Procedures:

(1) Transform E. coli cells with a recombinant plasmid;

(2) Pick single colonies into test tubes or shaking-bottles containing a desired medium;

(3) Incubate with shaking at the low temperature (e.g. 27° C.~35° C.) to early logarithmic phase. If necessary, inoculate and enlarge the culture before proceeding to the next step;

(4) Induce the gene expression by transferring the test tubes or flasks into a shaking water-bath incubator pre-heated to the high temperature 37° C.~44° C.; and continue to cultivate for 2~12 h as desired. Temperature change can also be manually achieved by holding and shaking the test tubes or flasks for about 10 min in a water bath of 37° C.~44° C. before cultivating in a shaking air-bath incubator at 37° C.~44° C., and (5) Harvest cells and isolate the recombinant protein as desired.

3. Induction of Gene Expression in Fermentor-Scales

For heat-shock induction in a larger or bulk volume of culture, this invention provides a method, which is designated "flow-in-heat." Similarly to the procedure described previously, freshly transformed E. coli cells are used to achieve the best expression level. The principal points of flow-in-heat are as follows:

(1) Take two fermentors A and B, use A at a lower temperature a, and B at a higher temperature b. Before cells are introduced to fermentor B, the time needed for raising temperature of a unit volume of medium in fermentor B from temperature a to b is determined, and the heating rate x (1/min), i.e. the amount of time needed for the temperature of a unit volume, e.g. 1, to be increased from a to b, is calculated. For temperature a, 27° C.-35° C. is recommended with 30° C. being preferred, and 37° C.-44° C. is recommended for temperature b with a preferred range of 40° C.-42° C.

(2) Add a suitable amount (n liters) of medium into fermentor A, and about n×0.1~1 liters into fermentor B, autoclave, and cool down to the temperature a and b, respectively.

(3) Inoculate fermentor A using E. coli cells carrying a recombinant plasmid of pHsh system, and cultivate with aerating and stirring at temperature a.

(4) When the cells grow to early logarithmic phase in fermentor A, induce gene expression by pumping the culture into fermentor B with a flow rate (1/min) corresponding to the heating rate determined in (1) above. In other words, if fermentor B can increase x liters of medium from temperature a to b per minute, then the flow rate should be adding x liters of medium from a to b per minute, while fermentor B is operating at the heating rate. The cell density in early logarithmic phase is varied with richness of the medium and strength of aeration, and in general the time to start expression induction is recommended at a cell density of about 10%~20% of the highest density.

(5) After all the culture has been pumped into B from A, continue to cultivate for 2-12 h at temperature b.

(6) Harvest cells and isolate the recombinant protein as desired.

Example 3

Expression of Gene xar or xyn in Vectors of Different Systems

1. Gene Cloning and Expression Assay

The arabinosidase gene xar (GenBank Accession No. AF135015) from *Thermoanaerobacter ethanolicus*, the xylanase gen xynB (GenBank Accession No. AE001693) from *T. maritima*, and its mutant xynIII were used as target genes for expression tests. In addition to pHsh, pTrc99A (lac/tac/trc system, Pharmacia, Piscataway, N.J., USA), pET28 (T7 system, Novagen, Inc., Madison, Wis., USA) and pJLA503 ($p_L$ system) were used as vectors. The target genes were cloned into the expression vectors using standard methods (Sambrook and Russell, 2001), and recombinant plasmids were constructed and recorded directly with their vector and gene names, which included pHsh-xynB, pHsh-xynIII, pHsh-xar, pET-xynIII, pET-xar, pTrc-xar, and pJLA-xynIII. The plasmids were introduced into E. coli strain JM109 (DE3) (for pET vector), or strain JM109 (for the others) by electroporation.

During the period of cultivation, cell densities were measured by $OD_{600}$ reading, and expression levels determined by enzyme activities. The xylanase activity was determined at 90° C., pH 5.8 using 0.5% xylan (Sigma, from oat spelt) as substrate, and the reducing equivalents released were quantified using p-hydroxybenzoic acid hydrazide (PAHBAH) assay (Lever, M. 1972. A new reaction for colorimetric determination of carbohydrates. Anal. Biochem. 47: 273). The arabinosidase activity was determined at 80° C. and pH 5.7 using p-nitrophenyl α-arabinofuranoside as substrate, and catalytic product, p-nitrophenol was quantified by reading absorbance at 405 nm after adding 2× volume of 1 M $Na_2CO_3$ into the reaction mixture. One unit of enzyme activity was defined as the amount of the enzyme to produce 1 µmol of products in a minute.

2. Induction of Xylanase Gene Expression by Flow-in-Heat

In a 15-liter fermentor, 10 liters of Terrific medium was cooled to 30° C. after autoclave, another 10 liter medium was in a 25-liter fermentor automatically controlled at 42° C., and 0.8 g of ampicillin was added into each fermentor. To the 15-liter fermentor, an inoculum of 250-ml culture of E. coli harboring pHsh-xynB was injected into its medium, and cells were grown aerobically at 250 rpm at 30° C. to $OD_{600}$=1.2. Then the culture was transferred into the 25-liter fermentor at a rate of 1 liter per min, where the temperature was kept at the level of 39° C.~42° C. by heating and stirring. The cultivation was continued aerobically at 42° C. after all the culture in the 15-liter fermentor was transferred into 25-liter fermentor, and cell density and xylanase activity were monitored every hour. The cells were harvested by centrifuge after 6 hours when the xylanase activity was about 240,000 U per liter of culture.

3. Expression in Shaking-Bottles

Expression of pHsh-xar, pHsh-xynIII and pJLA-xynIII was induced by heat shock as follows. Overnight cultures of *E. coli* carrying the above plasmids were inoculated into 30 ml of Terrific media containing 0.1 mg/ml of ampicillin in a 100-ml flask, and the cells were grown at 30° C. in a shaking incubator. When the cell density ($OD_{600}$) reached about 1.0, the flask was transferred into a water bath shaker of 42° C., in which cell growth was continued and gene expression is induced for up to 9 h. The expression of genes in pET-xar, pET-xynIII, or pTrc-xar was induced by adding IPTG to 1 or 5 mM according to manufacture's instructions.

Figure 2:
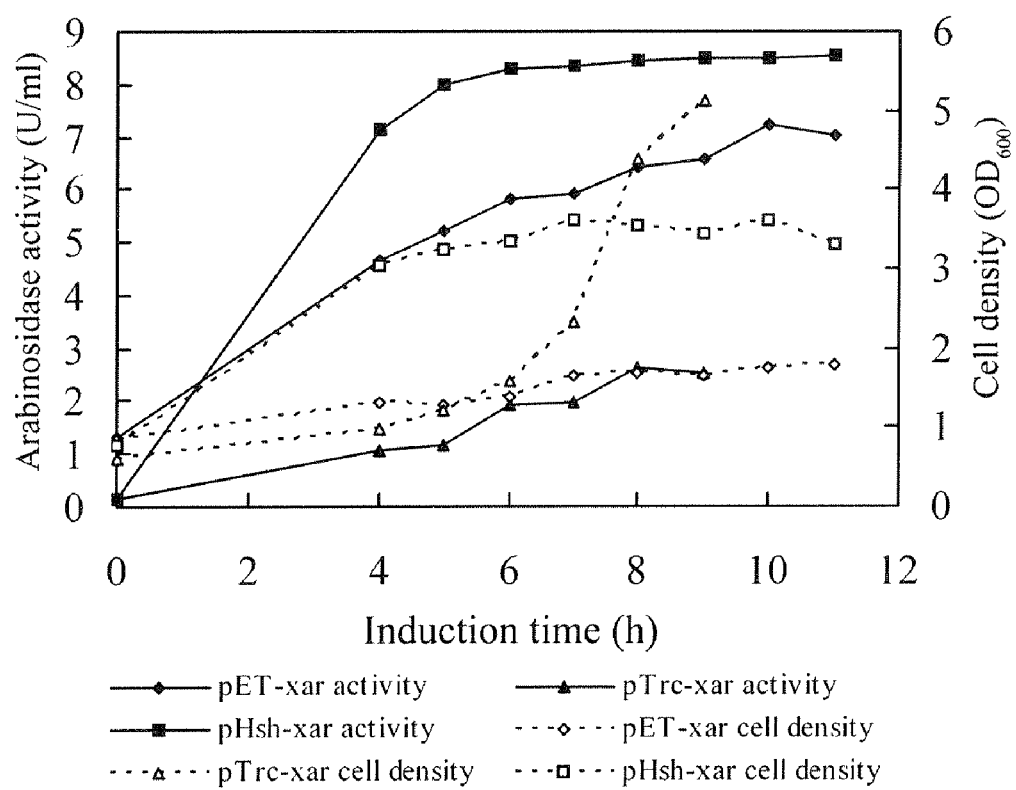
FIG. 2 shows the expression level of arabinofuranosidase and cell density of *E. coli* cells harboring different vectors at different time. The LB medium used contains the following antibiotics: for pHsh-xar, and pTrc99A-xar, ampicillin, 100 μg/ml; and for pET-xar kanamycin, 30 μg/ml; a unit of arabinofuranosidase activity is defined as follows: using 1 mM p-Nitrophenyl-α-L-arabinopyranoside (pNPA, sigma) as substrate, one unit of arabinofuranosidase activity is the amount of enzyme that catalyzes the production of 1 μmol of p-nitrophenol (pNP) in one minute under the conditions of 80° C. & pH=5.7.
Figure 3:
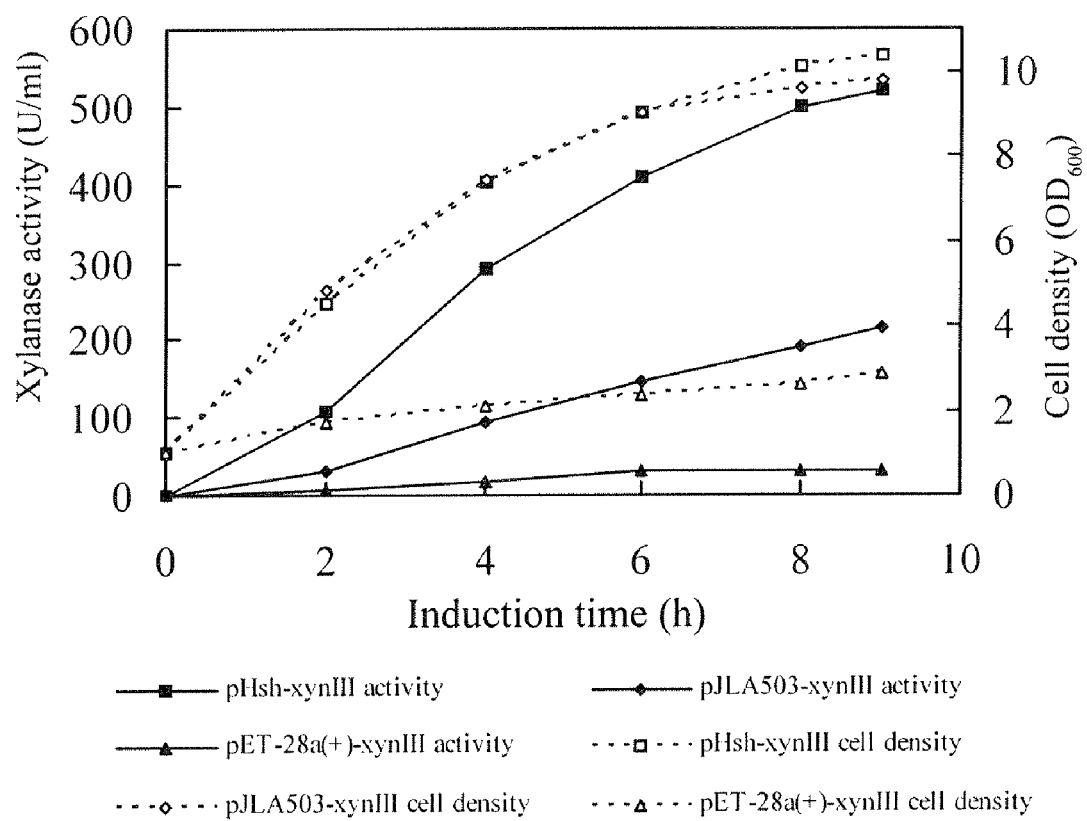
FIG. 3 shows the expression level of xylanase and cell density of *E. coli* cells harboring different vectors at different time. The LB medium used contains the following antibiotics: for pET-xynIII, kanamycin at 30 μg/ml; and for pJLA503-xynIII, and pHsh-xynIII, ampicillin at 100 μg/ml. One unit of xylanase activity is defined as the amount of enzyme that catalyzes the production of 1 μmol of reducing sugar using 0.5% xylan from oat spelts as substrate in one minute under the conditions of 90° C. & pH=5.8.

The expression levels were compared by arabinosidase activities in *E. coli* harboring pHsh-xar, pET-xar, and pTrc-xar, and by xylanase activities in cells harboring pHsh-xynIII, pET-xynIII, and pJLA-xynIII. The results showed that the arabinosidase activity produced by pHsh-xar was 3.6 and 1.5 times higher than that by pTrc-xar and pET-xar (FIG. 2), and the xylanase activity produced by pHsh-xynIII was 10 and 2.4 times higher than that by pET-xynIII and pJLA-xynIII (FIG. 3), respectively.

Examples 4-20

The following experiments were conducted using the vector(s), induction methods and target genes and host strains as described above in Examples 1-3, except otherwise and specifically noted.

Example 4

The host cell used was *E. coli* strain K12.

Example 5

The difference consisted in the method of induction. Here, the recombinant cells were cultivated aerobically in a shaker at 30° C. After the cell density reached an $OD_{600}$ of 0.8, the test tubes (or flasks) were transferred into the water-bathed shaker from 30° C. to 42° C., and continued to cultivate for 7 h.

Example 6

The difference consisted in the method of induction. Here, recombinant pHsh-xar cells were cultivated aerobically in a shaker at 30° C. After the cell density reached an $OD_{600}$ of 0.8, the cells were harvested by centrifugation, and removed the supernatant, the cell pellets were inoculated to the media which had been preheated to 40° C., and continued to cultivate for 8 h at 40° C.

Example 7

The difference consisted in the procedure of expression. Here, after autoclave, the temperature in fermentor A was decreased to 28° C., and the cells were cultivated to an $OD_{600}$ of 0.4. After autoclave, the temperature in fermentor B with 1 L sterile Terrific media was decreased to 37° C. When the cells grew to early logarithmic phase in fermentor A, induced gene expression by pumping the culture into fermentor B with a flow rate of 1 L/min. All the culture had been pumped into B from A, continued to cultivate for 2 h at 37° C.

Example 8

The difference consisted in the procedure of expression. Here, after autoclave, the temperature in fermentor A was decreased to 32° C., and the cells were cultivated to an $OD_{600}$ of 0.5. After autoclave, the temperature in fermentor B with 5 L sterile Terrific media was decreased to 44° C. When the cells grew to early logarithmic phase in fermentor A, induced gene expression by pumping the culture into fermentor B with a flow rate of 1 L/min. All the culture had been pumped into B from A, continued to cultivate for 10 h at 44° C.

Example 9

The difference consisted in the procedure of expression. Here, after autoclave, the temperature in fermentor A was decreased to 29° C., and the cells were cultivated to an $OD_{600}$ of 0.9. After autoclave, the temperature in fermentor B with 8 L sterile Terrific media was decreased to 41° C. When the cells grew to early logarithmic phase in fermentor A, induced gene expression by pumping the culture into fermentor B with a flow rate of 1 L/min. All the culture had been pumped into B from A, continued to cultivate for 9 h at 37° C.

Example 10

The difference consisted in the procedure of expression. Here, after autoclave, the temperature in fermentor A was decreased to 31° C., and the cells were cultivated to an $OD_{600}$ of 0.7. After autoclave, the temperature in fermentor B with 2 L sterile Terrific media was decreased to 40° C. When the cells grew to early logarithmic phase in fermentor A, induced gene expression by pumping the culture into fermentor B with a flow rate of 1 L/min. All the culture had been pumped into B from A, continued to cultivate for 12 h at 40° C.

Example 11

The difference consisted in the procedure of expression. Here, there were 15 L media in fermentor A, and there were 20 L media in fermentor B.

Example 12

The difference consisted in the procedure of expression. Here, there were 20 L media in fermentor A, and there were 15 L media in fermentor B.

Example 13

The difference consisted in the heating rate. Here, the heating rate in fermentor B was 1.2 L/min.

Example 14

The difference consisted in the opportunity of induction. Here, the induction is carried out when the cell density in fermentor A reached an $OD_{600}$ of 3.0.

Example 15

The difference consisted in the opportunity of induction. Here, the induction is carried out when the cell density in fermentor A reached an $OD_{600}$ of 0.7.

Example 16

The difference consisted in the opportunity of induction. Here, the induction is carried out when the cell density in fermentor A reached an $OD_{600}$ of 2.2.

Example 17

The difference consisted in the media which was used. Here, the cultivation was carried out in Luria-Bertani media.

Example 18

The difference consisted in the opportunity of induction. Here, the induction is carried out when the cell density in fermentor A reached an $OD_{600}$ of 2.0.

Example 19

The difference consisted in the opportunity of induction. Here, the induction is carried out when the cell density in fermentor A reached an $OD_{600}$ of 0.6.

Example 20

The difference consisted in the opportunity of induction. Here, the induction is carried out when the cell density in fermentor A reached an $OD_{600}$ of 0.9.

We claim:

1. An expression vector comprising a promoter that is recognized and regulated by a heat-shock sigma factor $\sigma^{32}$ of *Escherichia coli*, wherein the promoter comprises the nucleotide sequence SEQ ID NO: 1.

2. The expression vector according to claim 1, further comprising a polynucleotide sequence encoding a target polypeptide sequence under the control of the promoter.

3. The expression vector of claim 2, wherein the vector comprises the expression vector pHsh shown in FIG. 1A, wherein the Hsh promoter in FIG. 1A comprises the nucleotide sequence SEQ ID NO: 1, and the polynucleotide sequence encoding a target polypeptide is inserted in a multiple cloning site of vector pHsh as set forth in FIG. 1B.

4. A method for producing a polypeptide, the method comprising (a) providing bacterial cells comprising an expression vector which comprises a polynucleotide sequence encoding the polypeptide under the control of a promoter that is recognized by a heat shock sigma factor $\sigma^{32}$ of *Escherichia coli*, wherein the promoter comprises the nucleotide sequence SEQ ID NO: 1, and (b) cultivating the bacterial cells under conditions that induce the expression of the polynucleotide sequence in the vector.

5. The method according to claim 4, wherein the vector comprises the expression vector pHsh shown in FIG. 1A, wherein the Hsh promoter in FIG. 1A comprises the nucleotide sequence SEQ ID NO: 1, and the polynucleotide sequence encoding a target polypeptide is inserted in a multiple cloning site of vector pHsh as set forth in FIG. 1B.

6. The method according to claim 4, wherein the bacterial cells are *E. coli* cells.

7. The method according to claim 4, wherein said conditions that induce the expression of the polynucleotide sequence comprise subjecting the bacterial cells to a temperature shift.

* * * * *

```
                        SEQUENCE LISTING

<160> NUMBER OF SEQ ID NOS: 12

<210> SEQ ID NO 1
<211> LENGTH: 41
<212> TYPE: DNA
<213> ORGANISM: Artificial
<220> FEATURE:
<223> OTHER INFORMATION: Sigma 32 Promoter partial sequence

<400> SEQUENCE: 1 ccccct tgaa tgtgggggaa acatccccat gatccaagga g              41

<210> SEQ ID NO 2
<211> LENGTH: 40
<212> TYPE: DNA
<213> ORGANISM: E. coli

<400> SEQUENCE: 2
cggcgttgaa tgtgggggaa acatccccat atactgacgt                 40

<210> SEQ ID NO 3
<211> LENGTH: 40
<212> TYPE: DNA
<213> ORGANISM: E. coli

<400> SEQUENCE: 3 ccccttgat gacgtggttt acgaccccat ttagtagtca                  40

<210> SEQ ID NO 4
<211> LENGTH: 41
<212> TYPE: DNA
<213> ORGANISM: artificial
<220> FEATURE:
<223> OTHER INFORMATION: Hsh promoter

<400> SEQUENCE: 4 ccccct tgaa tgtgggggaa acatccccat gatccaagga g              41

<210> SEQ ID NO 5
<211> LENGTH: 32
<212> TYPE: DNA
<213> ORGANISM: Artificial
<220> FEATURE:
<223> OTHER INFORMATION: rho independent GAAA terminator
```

```
<400> SEQUENCE: 5
gaaggccgct tccgaaagga agcggctttt tt                                    32

<210> SEQ ID NO 6
<211> LENGTH: 46
<212> TYPE: DNA
<213> ORGANISM: Artificial
<220> FEATURE:
<223> OTHER INFORMATION: ECORPOC Terminator

<400> SEQUENCE: 6
cggacgtcag gccgccactt cggtgcggtt acgtccggct ttcttt                     46

<210> SEQ ID NO 7
<211> LENGTH: 44
<212> TYPE: DNA
<213> ORGANISM: Artificial
<220> FEATURE:
<223> OTHER INFORMATION: ECOXYLE Terminator

<400> SEQUENCE: 7
cttcctgtcc agcacgccgc gccatttcgg cgtgctgact tttt                       44

<210> SEQ ID NO 8
<211> LENGTH: 67
<212> TYPE: DNA
<213> ORGANISM: Artificial
<220> FEATURE:
<223> OTHER INFORMATION: forward primer

<400> SEQUENCE: 8
ccggaattcc tccttggatc atggggatgt ttcccccaca ttcaaggggg ctcttccgct      60
tcctctc                                                                67

<210> SEQ ID NO 9
<211> LENGTH: 58
<212> TYPE: DNA
<213> ORGANISM: Artificial
<220> FEATURE:
<223> OTHER INFORMATION: reverse primer

<400> SEQUENCE: 9
tgaagcttga aggccgcttc cgaaaggaag cggcttttt gcctgatgcg gtattttc         58

<210> SEQ ID NO 10
<211> LENGTH: 191
<212> TYPE: DNA
<213> ORGANISM: artificial
<220> FEATURE:
<223> OTHER INFORMATION: pHsh regulatory region

<400> SEQUENCE: 10
aagcggaaga gccccttga atgtggggga aacatcccca tgatccaatg acctgttaac       60
cgtcgacaag aaggagatat acccatggag gcctctagac tgcagcggcc gcatgcatat     120
ggatctcgag caccaccacc accaccacta ataagcttga aggccgcttc cgaaaggaag     180 cggcttttt g                                                           191

<210> SEQ ID NO 11
<211> LENGTH: 30
<212> TYPE: DNA
<213> ORGANISM: artificial
<220> FEATURE:
<223> OTHER INFORMATION: consensus promoter sequence
```

```
<220> FEATURE:
<221> NAME/KEY: misc_feature
<222> LOCATION: (7)..(25)
<223> OTHER INFORMATION: n is a, c, g or t, and may contain up to two
      deletions

<400> SEQUENCE: 11
ttgacannnn nnnnnnnnnn nnnntataat                                       30

<210> SEQ ID NO 12
<211> LENGTH: 35
<212> TYPE: DNA
<213> ORGANISM: artificial
<220> FEATURE:
<223> OTHER INFORMATION: consensus promoter
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (13)..(27)
<223> OTHER INFORMATION: n is a, c, g or t, and may contain up to two
      deletions
<220> FEATURE:
<221> NAME/KEY: misc_feature
<222> LOCATION: (34)..(34)
<223> OTHER INFORMATION: n is a, c, g, or t

<400> SEQUENCE: 12
nncncncttg aannnnnnnn nnnnnnnccc catnt                                 35
```